(12) United States Patent
Loebl et al.

(10) Patent No.: US 9,737,411 B2
(45) Date of Patent: Aug. 22, 2017

(54) WORM-GEAR ACTUATED ORTHOPEDIC IMPLANTS AND METHODS

(71) Applicant: NLT SPINE LTD., Kfar Saba (IL)

(72) Inventors: Oded Loebl, Tel Mond (IL); Haim Yustein, Netanya (IL); Didier Toubia, Raanana (IL)

(73) Assignee: NLT SPINE LTD., Kfar Saba (IL)

( * ) Notice: Subject to any disclaimer, the term of this patent is extended or adjusted under 35 U.S.C. 154(b) by 227 days.

(21) Appl. No.: 14/412,447

(22) PCT Filed: Dec. 11, 2014

(86) PCT No.: PCT/IB2014/066823
§ 371 (c)(1),
(2) Date: Jan. 1, 2015

(87) PCT Pub. No.: WO2015/087285
PCT Pub. Date: Jun. 18, 2015

(65) Prior Publication Data
US 2016/0324654 A1   Nov. 10, 2016

Related U.S. Application Data

(60) Provisional application No. 61/914,435, filed on Dec. 11, 2013, provisional application No. 61/951,566, filed on Mar. 12, 2014.

(51) Int. Cl.
*A61F 2/44* (2006.01)
*A61F 2/30* (2006.01)

(52) U.S. Cl.
CPC .......... *A61F 2/4425* (2013.01); *A61F 2/4455* (2013.01); *A61F 2/4465* (2013.01);
(Continued)

(58) Field of Classification Search
CPC .. A61F 2002/30523; A61F 2002/30471; A61F 2002/30509; A61B 17/7065
See application file for complete search history.

(56) References Cited

U.S. PATENT DOCUMENTS 4,759,769 A   7/1988   Hedman et al.
5,059,193 A   10/1991  Kuslich
(Continued)

FOREIGN PATENT DOCUMENTS

DE   2263842   7/1974
DE   9107494   9/1991
(Continued)

OTHER PUBLICATIONS

E. AliCl, et al "Prostheses Designed For Vertebral Body Replacement" in Journal of Biomechanics vol. 23 1990, No. 8. pp. 799-809.

*Primary Examiner* — Jan Christopher Merene
*Assistant Examiner* — Atiya Mahmud
(74) *Attorney, Agent, or Firm* — Mark M. Friedman

(57) ABSTRACT

An intervertebral implant has at least one arm (14) pivotally connected to a base (10). At least one worm gear configuration includes a worm in (18) mounted within the base (10) so as to be rotatable, and a set of gear teeth (20) associated with the arm (14). When the worm (18) is rotated about its central axis, the arm (14) is driven through a range of pivotal motion relative to the base so as to change an angle of inclination between a direction of elongation (16) of the arm and the direction of elongation (12) of the base. Embodiments of the invention include devices with a hollow proximal worm allowing access into the implant via the worm, distally deployed worms, and devices with a pair of worm gear assemblies that operate synchronously or independently.

6 Claims, 14 Drawing Sheets

(52) U.S. Cl.
CPC ............... *A61F 2002/30471* (2013.01); *A61F 2002/30525* (2013.01); *A61F 2002/30538* (2013.01); *A61F 2002/30556* (2013.01); *A61F 2002/30579* (2013.01); *A61F 2002/30904* (2013.01)

(56) References Cited

U.S. PATENT DOCUMENTS

| | | |
|---|---|---|
| 5,171,278 A | 12/1992 | Pisharodi |
| 5,258,031 A | 11/1993 | Salib et al. |
| 5,390,683 A | 2/1995 | Pisharodi |
| 5,534,029 A | 7/1996 | Shima |
| 5,599,279 A | 2/1997 | Slotman |
| 5,620,458 A | 4/1997 | Green et al. |
| 6,039,761 A | 3/2000 | Li et al. |
| 6,080,193 A | 6/2000 | Hochshuler et al. |
| 6,126,689 A | 10/2000 | Brett |
| 6,190,414 B1 | 2/2001 | Young et al. |
| 6,238,403 B1 | 5/2001 | Greene, Jr. et al. |
| 6,332,894 B1 | 12/2001 | Stalcup et al. |
| 6,375,682 B1 | 4/2002 | Fleischmann et al. |
| 6,387,130 B1 | 5/2002 | Stone et al. |
| 6,419,705 B1 | 7/2002 | Erickson |
| 6,443,989 B1 | 9/2002 | Jackson |
| 6,491,724 B1 | 12/2002 | Ferree |
| 6,576,016 B1 | 6/2003 | Hochshuler et al. |
| 6,582,451 B1 | 6/2003 | Marucci et al. |
| 6,620,196 B1 | 9/2003 | Trieu |
| 6,641,614 B1 | 11/2003 | Wagner et al. |
| 6,676,665 B2 | 1/2004 | Foley |
| 6,706,070 B1 | 3/2004 | Wagner et al. |
| 6,830,589 B2 | 12/2004 | Erickson |
| 7,070,598 B2 | 7/2006 | Lim et al. |
| 7,087,055 B2 | 8/2006 | Lim et al. |
| 7,097,648 B1 | 8/2006 | Globerman et al. |
| 7,431,735 B2 | 10/2008 | Liu et al. |
| 7,625,377 B2 | 12/2009 | Veldhuizen et al. |
| 7,655,046 B2 | 2/2010 | Dryer et al. |
| 7,720,282 B2 | 5/2010 | Blake et al. |
| 7,763,028 B2 | 7/2010 | Lim et al. |
| 7,799,081 B2 | 9/2010 | McKinley |
| 7,846,206 B2 | 12/2010 | Oglaza et al. |
| 7,901,409 B2 | 3/2011 | Canaveral |
| 7,905,920 B2 | 3/2011 | Galea |
| 7,909,872 B2 | 3/2011 | Zipnick et al. |
| 7,938,860 B2 | 5/2011 | Trieu |
| 7,947,078 B2 | 5/2011 | Siegal |
| 7,959,652 B2 | 6/2011 | Zucherman et al. |
| 8,021,429 B2 | 9/2011 | Viker |
| 8,025,665 B2 | 9/2011 | Lim et al. |
| 8,062,375 B2 | 11/2011 | Glerum et al. |
| 8,100,972 B1* | 1/2012 | Bruffey ............... A61F 2/442 623/17.11 |
| 8,123,809 B2 | 2/2012 | Melkent et al. |
| 8,133,232 B2 | 3/2012 | Levy et al. |
| 8,187,332 B2 | 5/2012 | McLuen |
| 8,292,963 B2 | 10/2012 | Miller et al. |
| 8,303,658 B2 | 11/2012 | Peterman |
| 8,308,802 B2 | 11/2012 | Rhoda et al. |
| 8,317,798 B2 | 11/2012 | Lim et al. |
| 8,317,802 B1 | 11/2012 | Manzi et al. |
| 8,317,866 B2 | 11/2012 | Palmatier et al. |
| 8,323,344 B2 | 12/2012 | Galeey et al. |
| 8,337,531 B2 | 12/2012 | Johnson et al. |
| 8,337,559 B2 | 12/2012 | Hanseel et al. |
| 8,343,193 B2 | 1/2013 | Johnson et al. |
| 8,349,013 B2 | 1/2013 | Zucherman et al. |
| 8,349,014 B2 | 1/2013 | Barreiro et al. |
| 8,377,071 B2 | 2/2013 | Lim et al. |
| 8,398,713 B2 | 3/2013 | Weiman |
| 8,403,990 B2 | 3/2013 | Dryer et al. |
| 8,444,697 B1 | 5/2013 | Butler et al. |
| 8,518,120 B2 | 8/2013 | Glerum et al. |
| 8,523,944 B2 | 9/2013 | Jimenez et al. |
| 8,556,979 B2 | 10/2013 | Glerum et al. |
| 8,579,907 B2 | 11/2013 | Lim et al. |
| 8,628,576 B2 | 1/2014 | Triplett et al. |
| 8,628,577 B1 | 1/2014 | Jimenez |
| 8,679,183 B2 | 3/2014 | Glerum et al. |
| 8,685,098 B2 | 4/2014 | Glerum et al. |
| 8,709,086 B2 | 4/2014 | Glerum |
| 8,771,360 B2 | 7/2014 | Jimenez et al. |
| 8,870,959 B2 | 10/2014 | Arnin |
| 9,017,413 B2 | 4/2015 | Siegal |
| 2002/0151976 A1 | 10/2002 | Foley et al. |
| 2003/0236520 A1 | 12/2003 | Lim et al. |
| 2004/0059418 A1 | 3/2004 | McKay et al. |
| 2004/0133280 A1 | 7/2004 | Trieu |
| 2004/0162618 A1 | 8/2004 | Mujwid et al. |
| 2004/0193158 A1 | 9/2004 | Lim et al. |
| 2005/0113920 A1 | 5/2005 | Foley et al. |
| 2005/0125062 A1 | 6/2005 | Biedermann |
| 2005/0143827 A1 | 6/2005 | Globerman et al. |
| 2005/0182416 A1 | 8/2005 | Lim |
| 2005/0209698 A1 | 9/2005 | Gordon |
| 2005/0228391 A1 | 10/2005 | Levy |
| 2005/0261683 A1 | 11/2005 | Veldhuzien |
| 2005/0278036 A1 | 12/2005 | Leonard et al. |
| 2006/0004455 A1 | 1/2006 | Leonard et al. |
| 2006/0041258 A1 | 2/2006 | Galea |
| 2006/0085070 A1 | 4/2006 | Kim |
| 2006/0142858 A1 | 6/2006 | Colleran et al. |
| 2006/0224241 A1 | 10/2006 | Butler et al. |
| 2006/0235423 A1 | 10/2006 | Cantu |
| 2006/0247778 A1 | 11/2006 | Ferree et al. |
| 2007/0032791 A1 | 2/2007 | Greenhalgh |
| 2007/0073398 A1 | 3/2007 | Fabian et al. |
| 2007/0123986 A1 | 5/2007 | Schaller |
| 2007/0173939 A1 | 7/2007 | Kim et al. |
| 2007/0233245 A1 | 10/2007 | Trieu et al. |
| 2007/0282449 A1 | 12/2007 | de Villiers |
| 2008/0119853 A1 | 5/2008 | Felt et al. |
| 2008/0125865 A1 | 5/2008 | Abdelgany |
| 2008/0243255 A1 | 10/2008 | Butler et al. |
| 2008/0312743 A1 | 12/2008 | Vila et al. |
| 2009/0216274 A1 | 8/2009 | Morancy-Meister et al. |
| 2009/0270873 A1 | 10/2009 | Fabian |
| 2010/0131009 A1 | 5/2010 | Roebling et al. |
| 2010/0274357 A1* | 10/2010 | Miller ............... A61F 2/44 623/17.16 |
| 2010/0286787 A1 | 11/2010 | Villiers et al. |
| 2011/0138948 A1* | 6/2011 | Jimenez ............... F16H 25/2056 74/424.82 |
| 2011/0172710 A1* | 7/2011 | Thommen ............ A61B 17/7065 606/249 |
| 2011/0172719 A1* | 7/2011 | Gorhan ............... A61B 17/8038 606/305 |
| 2011/0276141 A1 | 11/2011 | Caratsch |
| 2012/0004732 A1 | 1/2012 | Joel |
| 2012/0083889 A1 | 4/2012 | Purcell et al. |
| 2012/0123546 A1 | 5/2012 | Medina |
| 2012/0259416 A1 | 10/2012 | Blackwell et al. |
| 2013/0041471 A1 | 2/2013 | Siegal et al. |
| 2013/0066374 A1 | 3/2013 | Galeey et al. |
| 2013/0079883 A1* | 3/2013 | Butler ............... A61F 2/4425 623/17.16 |
| 2013/0158664 A1* | 6/2013 | Palmatier ............... A61F 2/447 623/17.16 |
| 2013/0158665 A1 | 6/2013 | Josse et al. |
| 2013/0158669 A1 | 6/2013 | Sangarian et al. |
| 2013/0317615 A1 | 11/2013 | Jimenez et al. |
| 2013/0325128 A1 | 12/2013 | Perloff et al. |
| 2014/0052254 A1 | 2/2014 | Glerum et al. |
| 2014/0114429 A1 | 4/2014 | Slone et al. |
| 2014/0156007 A1 | 6/2014 | Pabst et al. |
| 2014/0188225 A1 | 7/2014 | Klaus |
| 2014/0243982 A1 | 8/2014 | Miller |
| 2014/0249629 A1 | 9/2014 | Moskowitz |

FOREIGN PATENT DOCUMENTS

| | | |
|---|---|---|
| DE | 4416605 | 6/1995 |
| FR | 2717068 | 9/1995 |

(56) References Cited

FOREIGN PATENT DOCUMENTS

| | | |
|---|---|---|
| JP | 2004530527 | 10/2004 |
| JP | 2008512218 | 4/2008 |
| JP | 2011120957 | 6/2011 |
| WO | 98/34552 | 8/1998 |
| WO | 03003951 | 1/2003 |
| WO | 2008084479 | 7/2008 |
| WO | 2012011078 | 7/2011 |
| WO | 2013052807 | 4/2013 |

* cited by examiner

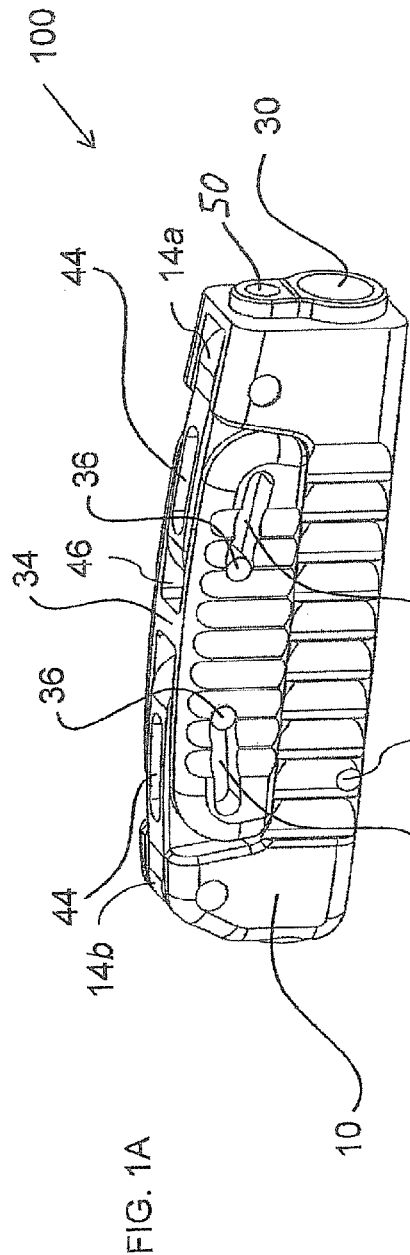
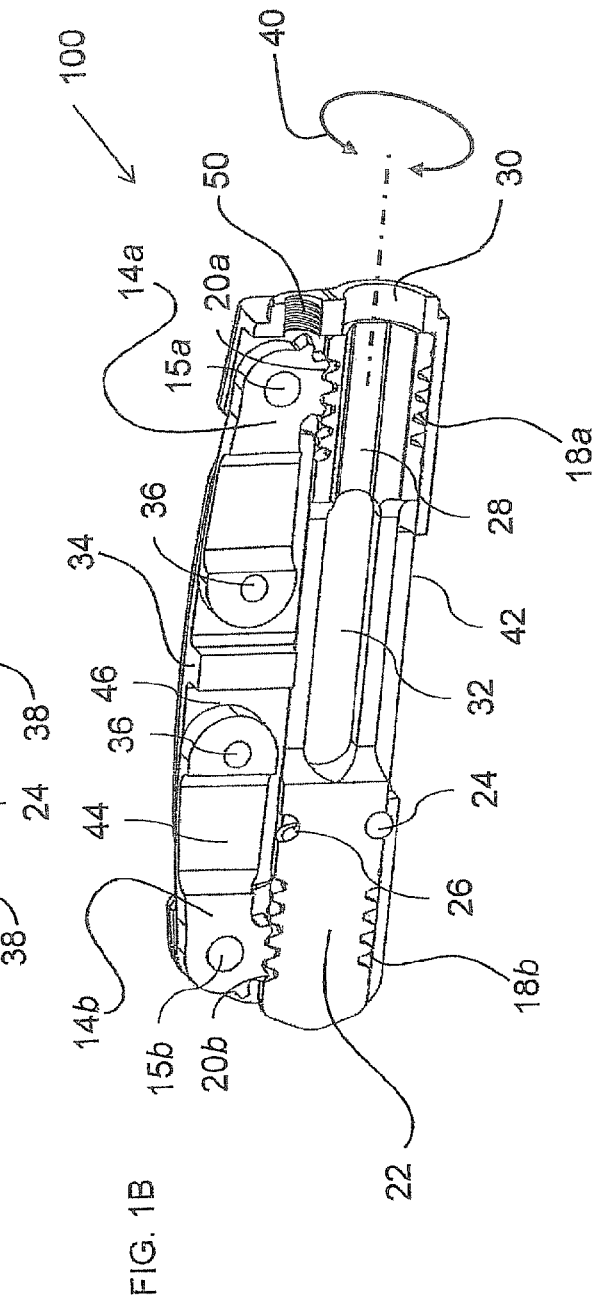
FIG. 1A
FIG. 1B

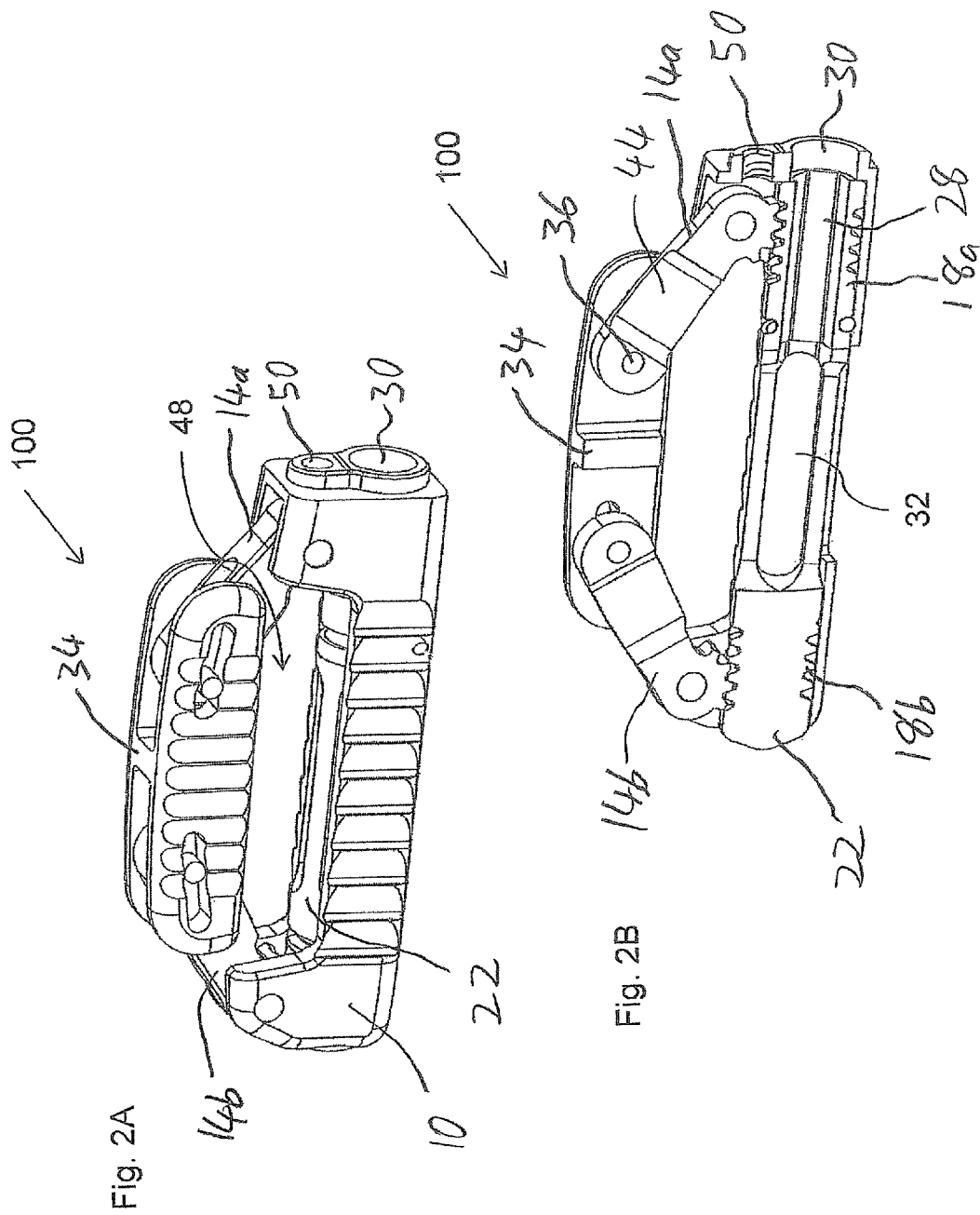

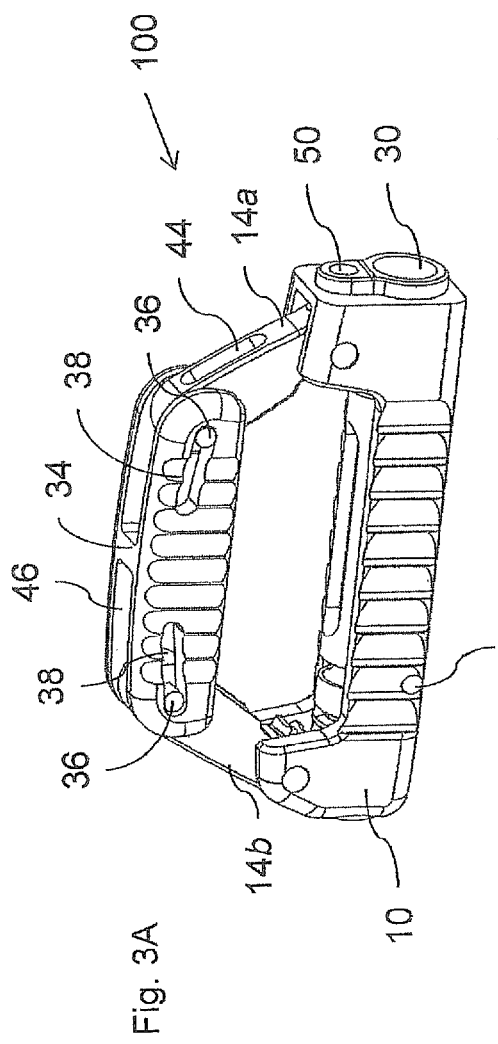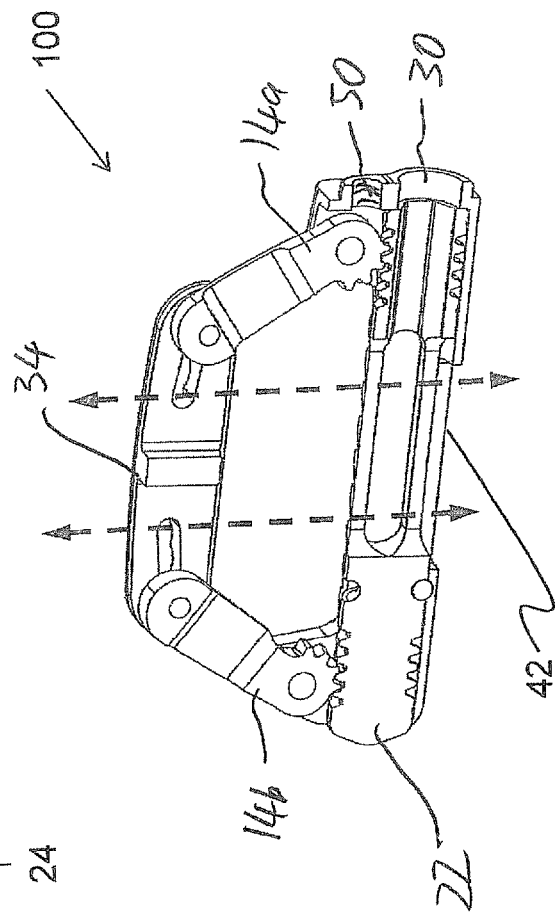

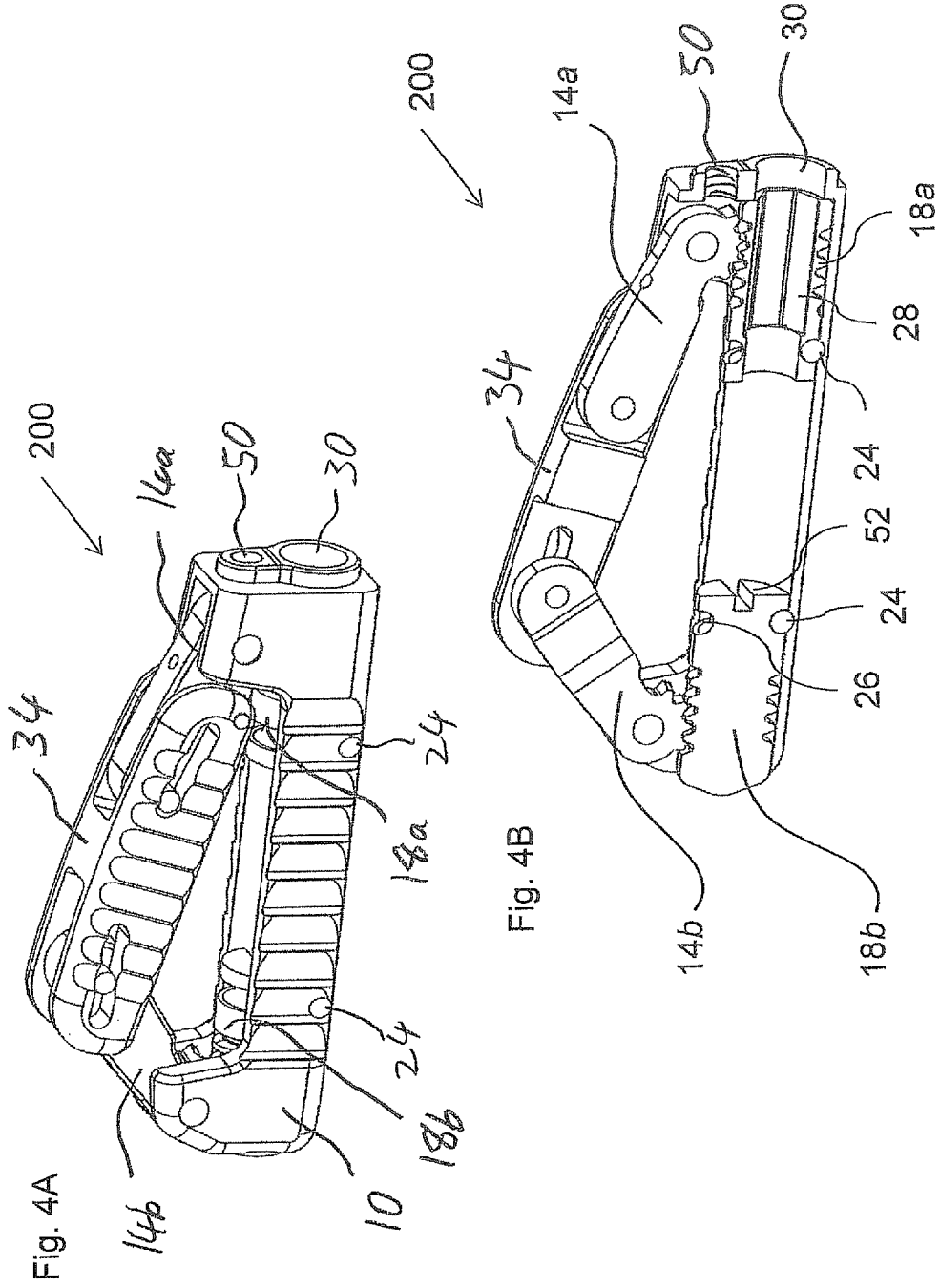

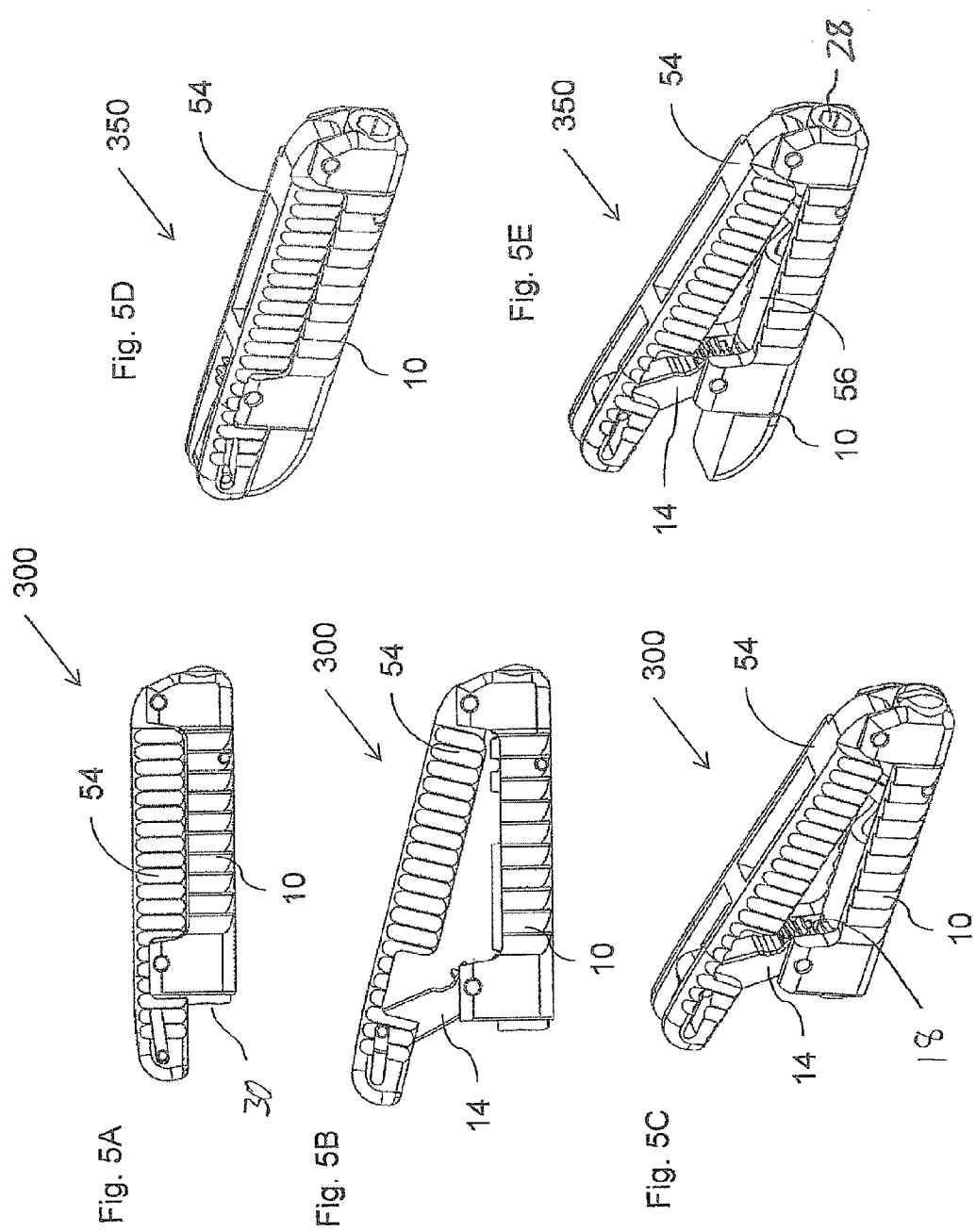

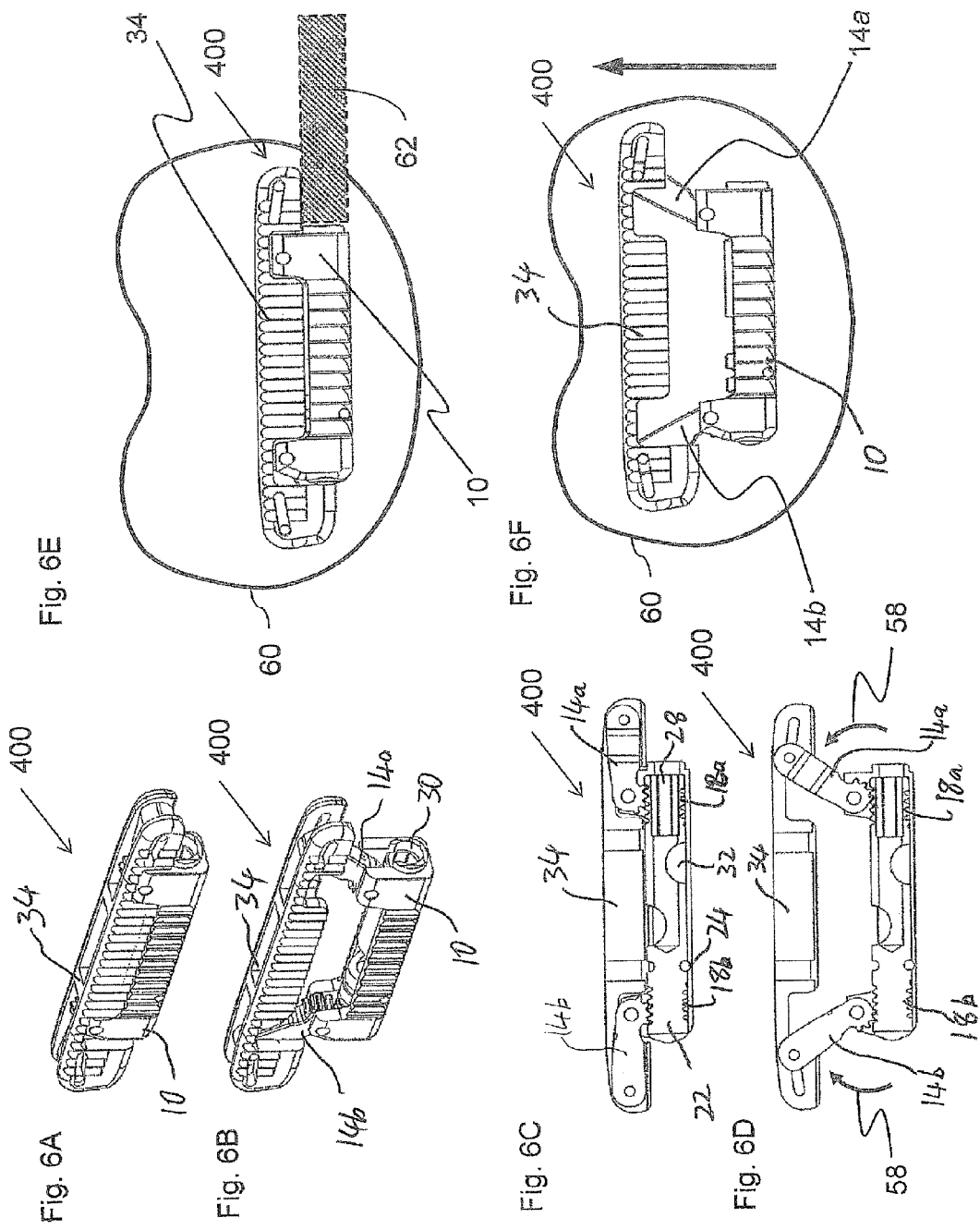

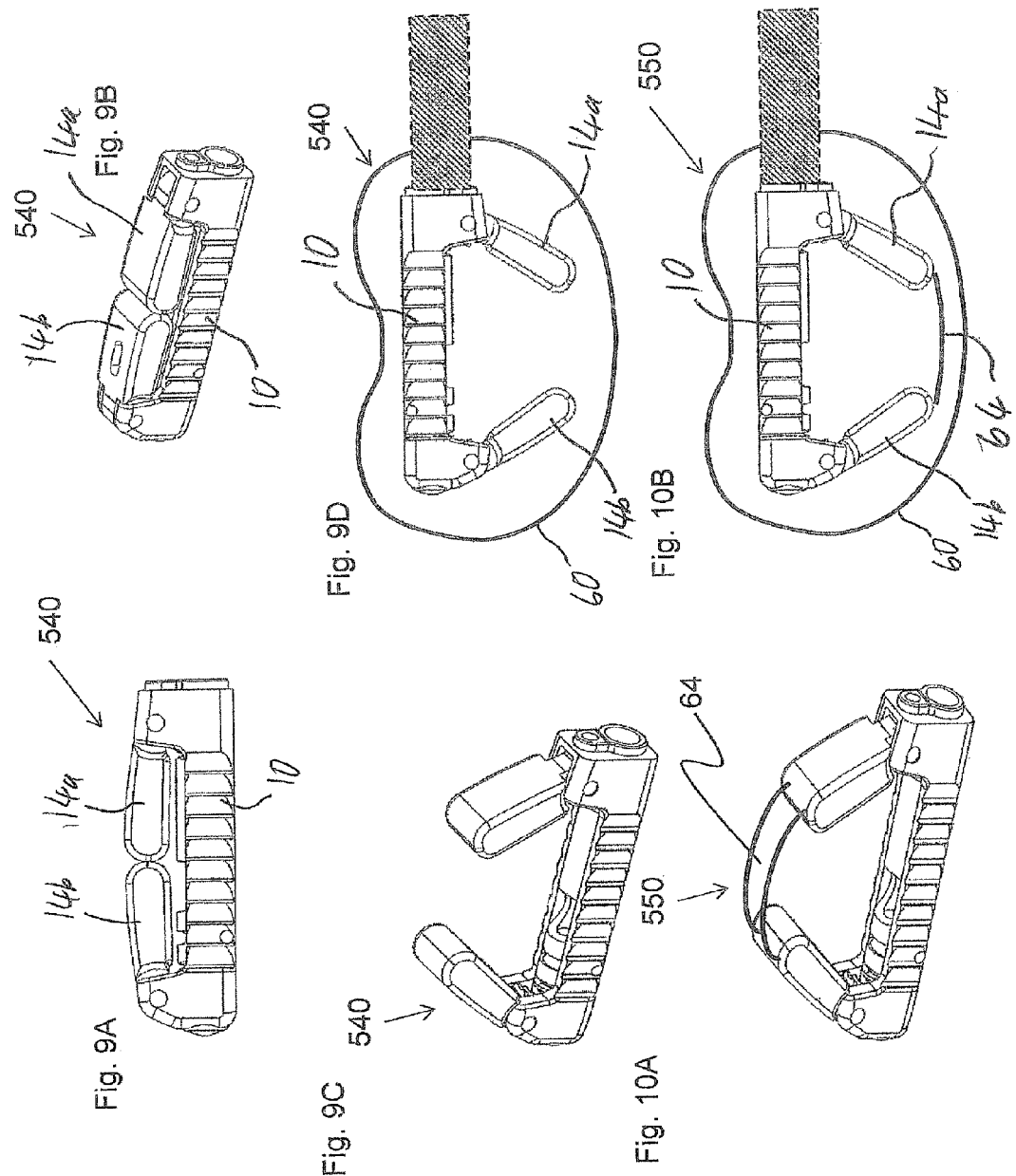

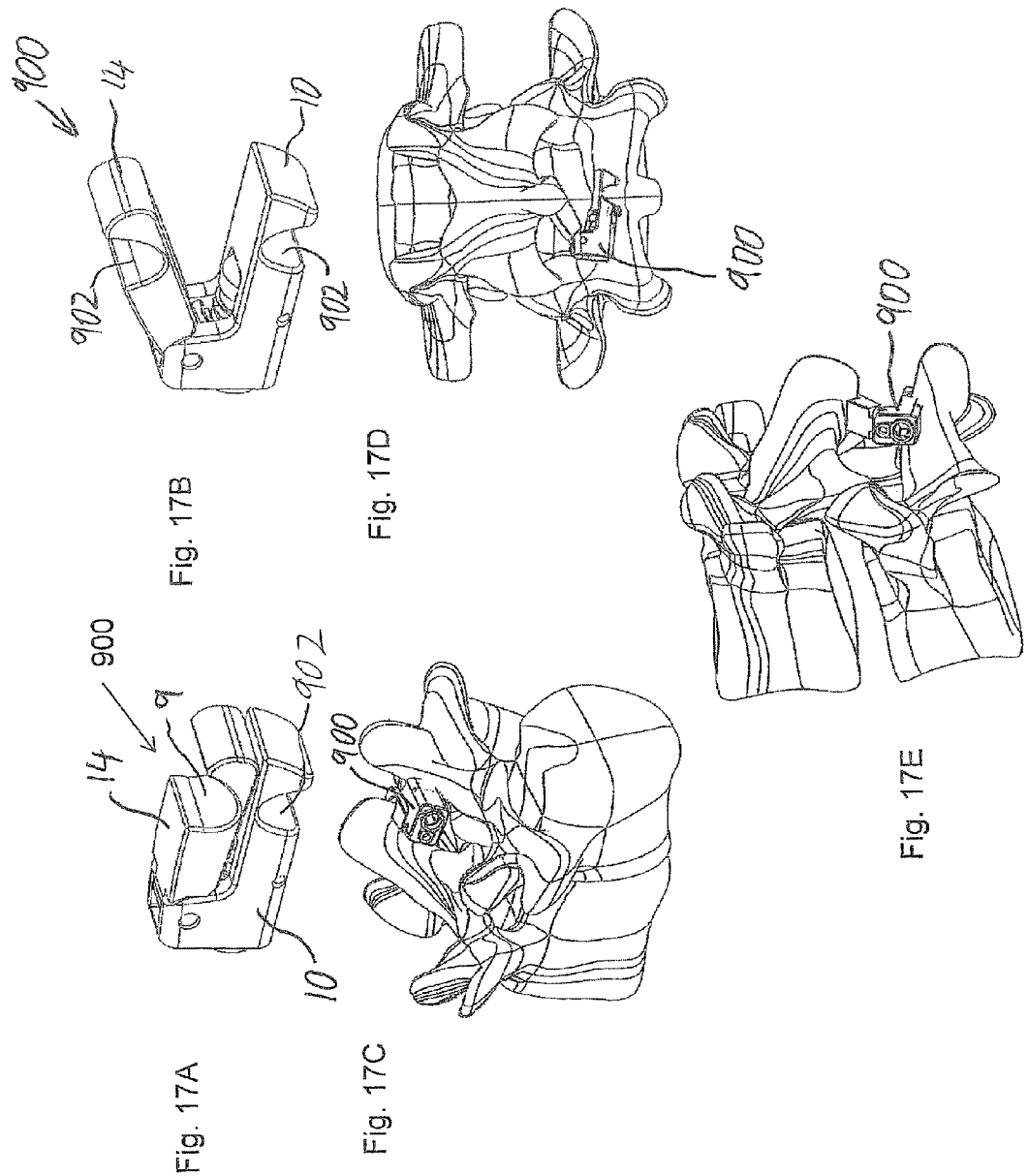

WORM-GEAR ACTUATED ORTHOPEDIC IMPLANTS AND METHODS

FIELD AND BACKGROUND OF THE INVENTION

The present invention relates to orthopedic implants and, in particular, it concerns orthopedic implants and corresponding methods in which a change of form of the implant is achieved after insertion of the implant by operation of one or more worm gear.

It is known to provide various types of orthopedic implant which change form after insertion, typically to allow introduction of the implant into the body in a collapsed or small-cross-section form prior to deployment of the implant within the body. Various deployment mechanisms are used to effect the change of form during or after introduction of the implant into the body.

US Patent Application Pre-Grant Publication No. US 2013/0079883 A1 to Butler et al. discloses an expandable spinal interbody device with a worm gear deployment mechanism. A small solid worm element in a blind hole at the proximal side of the implant engages teeth at the base of a pivotally mounted arm to effect lateral displacement of the arm.

SUMMARY OF THE INVENTION

The present invention is an orthopedic implant and corresponding method in which a change of form of the implant is achieved after insertion of the implant by operation of one or more worm gear.

According to the teachings of the present invention there is provided, a device comprising: (a) a base having a length defining a direction of elongation of the base; (b) an arm pivotally connected to the base, the arm having a length defining a direction of elongation of the arm; (c) a worm gear configuration comprising: (i) a worm mounted within the base so as to be rotatable about a central axis of the worm, and (ii) a set of gear teeth associated with the arm, the set of gear teeth being deployed to sequentially engage, and be driven by, the worm, such that, when the worm is rotated about its central axis, the arm is driven through a range of pivotal motion relative to the base so as to change an angle of inclination between the direction of elongation of the arm and the direction of elongation of the base, wherein the device is at least part of an orthopedic implant, and wherein the worm is hollow along at least part of a length of the worm so as to define part of a filling channel for introducing biocompatible material into the orthopedic implant.

According to a further feature of an embodiment of the present invention, the arm has a region distanced from the pivotal connection by at least half the length of the arm, the device further comprising a displaceable element, the displaceable element being interconnected with the region of the arm such that displacement of the arm through the range of pivotal motion from an initial position towards a final position causes displacement of at least part of the displaceable portion away from the base.

According to a further feature of an embodiment of the present invention, the displaceable element is interconnected with the region of the arm via a pin-and-slot engagement.

According to a further feature of an embodiment of the present invention, the displaceable element is pivotally interconnected with the base.

According to a further feature of an embodiment of the present invention, a second aim interconnects the displaceable element with the base, the second arm being pivotally interconnected with the base.

According to a further feature of an embodiment of the present invention, there is also provided a second worm gear configuration deployed for driving motion of the second arm relative to the base.

According to a further feature of an embodiment of the present invention, where the arm is referred to as the first arm and the worm is referred to as the first worm, there is also provided: (a) a second arm pivotally connected to the base, the second arm having a length defining a direction of elongation of the second arm; (b) a second worm gear configuration comprising: (i) a second worm mounted within the base so as to be rotatable about a central axis of the second worm, and (ii) a set of gear teeth associated with the second arm, the set of gear teeth being deployed to sequentially engage, and be driven by, the second worm, such that, when the second worm is rotated about its central axis, the second arm is driven through a range of pivotal motion relative to the base so as to change an angle of inclination between the direction of elongation of the second arm and the direction of elongation of the base.

According to a further feature of an embodiment of the present invention, the first worm and the second worm are integrated into a common actuator element so as to rotate together about a common central axis, and wherein the first and second worms have opposing helical handedness and are configured such that, on rotation of the common actuator element, the first and second arms are driven simultaneously in opposing rotation.

According to a further feature of an embodiment of the present invention, the first worm and the second worm are deployed coaxially and are independently rotatable, and wherein the second worm is configured to be rotated by engagement of an actuating tool inserted via the part of the filling channel passing through the first worm.

According to a further feature of an embodiment of the present invention, there is also provided a bridging element bridging between the first and second arms.

According to a further feature of an embodiment of the present invention, the bridging element is a rigid bridging element, and wherein the bridging element is interconnected with at least one of the first and second arms via a pin-and-slot engagement.

According to a further feature of an embodiment of the present invention, the bridging element is a flexible bridging element.

According to a further feature of an embodiment of the present invention, where the arm is referred to as the first arm, there is also provided: (a) a second arm pivotally connected to the base, the second arm having a length defining a direction of elongation of the second arm; (b) a set of gear teeth associated with the second aim, the set of gear teeth being deployed to sequentially engage, and be driven by, the worm, wherein the first aim and the second arm are deployed on opposite sides of the base such that, when the worm is rotated about its central axis, the first and second arms are driven simultaneously through a range of pivotal motion in opposite directions.

According to a further feature of an embodiment of the present invention, where the worm is referred to as the first worm, there is also provided: (a) a third arm pivotally connected to the base; (b) a fourth arm pivotally connected to the base; (c) a second worm gear configuration comprising: (i) a second worm mounted within the base so as to be rotatable about a central axis of the second worm, and (ii) a set of gear teeth associated with each of the third and the fourth arms, the set of gear teeth being deployed to sequentially engage, and be driven by, the second worm, wherein the third arm and the fourth arm are deployed on opposite sides of the base such that, when the second worm is rotated about its central axis, the third and fourth arms are driven simultaneously through a range of pivotal motion in opposite directions.

There is also provided according to the teachings of an embodiment of the present invention, a device comprising: (a) a base having a length defining a direction of elongation of the base; (b) a first arm pivotally connected to the base, the first arm having a length defining a direction of elongation of the first arm; (c) a second arm pivotally connected to the base, the second arm having a length defining a direction of elongation of the second arm; (d) a first worm gear configuration comprising: (i) a first worm mounted within the base so as to be rotatable about a central axis of the first worm, and (ii) a set of gear teeth associated with the first arm, the set of gear teeth being deployed to sequentially engage, and be driven by, the first worm; and (e) a second worm gear configuration comprising: (i) a second worm mounted within the base so as to be rotatable about a central axis of the second worm, and (ii) a set of gear teeth associated with the second arm, the set of gear teeth being deployed to sequentially engage, and be driven by, the second worm, such that rotation of the first and second worms about their central axes drives the first and second arms through respective ranges of pivotal motion relative to the base so as to change angles of inclination between the directions of elongation of the first and second arms and the direction of elongation of the base, wherein the device is at least part of an orthopedic implant.

According to a further feature of an embodiment of the present invention, the first worm and the second worm are deployed coaxially.

According to a further feature of an embodiment of the present invention, the first worm and the second worm are integrated into a common actuator element so as to rotate together about a common central axis, and wherein the first and second worms have opposing helical handedness and are configured such that, on rotation of the common actuator element, the first and second arms are driven simultaneously in opposing rotation.

According to a further feature of an embodiment of the present invention, the first worm and the second worm are deployed coaxially and are independently rotatable, and wherein the first worm is formed with an inner access channel for allowing insertion of an actuating tool for rotating the second worm via the inner access channel of the first worm.

According to a further feature of an embodiment of the present invention, there is also provided a bridging element bridging between the first and second arms.

According to a further feature of an embodiment of the present invention, the bridging element is a rigid bridging element, and wherein the bridging element is interconnected with at least one of the first and second arms via a pin-and-slot engagement.

According to a further feature of an embodiment of the present invention, the bridging element is a flexible bridging element.

There is also provided according to the teachings of an embodiment of the present invention, a device comprising: (a) a base having a length defining a direction of elongation of the base; (b) an aim pivotally connected to the base, the arm having a length defining a direction of elongation of the arm; (c) a worm gear configuration comprising: (i) a worm mounted within the base so as to be rotatable about a central axis of the worm, and (ii) a set of gear teeth associated with the arm, the set of gear teeth being deployed to sequentially engage, and be driven by, the worm, such that, when the worm is rotated about its central axis, the arm is driven through a range of pivotal motion relative to the base so as to change an angle of inclination between the direction of elongation of the arm and the direction of elongation of the base, wherein the device is at least part of an orthopedic implant, and wherein the worm is located in a distal half of the base.

BRIEF DESCRIPTION OF THE DRAWINGS

The invention is herein described, by way of example only, with reference to the accompanying drawings, wherein:

FIG. 1A is an isometric view of an orthopedic implant, constructed and operative according to an embodiment of the present invention, shown in a low profile closed state;

FIG. 1B is an isometric view similar to FIG. 1A cut away along a longitudinal central plane of the implant;

FIGS. 2A and 2B are views similar to FIGS. 1A and 1B, respectively, showing the implant in a first deployed state;

FIGS. 3A and 3B are views similar to FIGS. 1A and 1B, respectively, showing the implant in a further deployed state;

FIG. 4A is an isometric view of an orthopedic implant, constructed and operative according to an embodiment of the present invention, shown in an asymmetrically deployed state;

FIG. 4B is an isometric view similar to FIG. 4A cut away along a longitudinal central plane of the implant;

FIGS. 5A and 5B are side views of an orthopedic implant, constructed and operative according to an embodiment of the present invention, shown in a low profile closed state and a deployed state, respectively;

FIG. 5C is an isometric view of the deployed orthopedic implant of FIG. 5B;

FIGS. 5D and 5E are isometric views of an orthopedic implant, constructed and operative according to an embodiment of the present invention, shown in a low profile closed state and a deployed state, respectively;

FIGS. 6A and 6B are isometric views of an orthopedic implant, constructed and operative according to an embodiment of the present invention, shown in a low profile closed state and a deployed state, respectively;

FIGS. 6C and 6D are center-plane cross-sectional views taken through the implant of FIGS. 6A and 6B in the low profile closed state and the deployed state, respectively;

FIGS. 6E and 6F are schematic plan views illustrating the inserted state and the deployed state of the implant of FIGS. 6A and 6B used in a method for interbody fusion according to the teachings of the present invention;

FIG. 9A is a side view of an orthopedic implant, constructed and operative according to an embodiment of the present invention, shown in a low profile closed state;

FIGS. 9B and 9C are isometric views of the implant of FIG. 9A shown in a low profile closed state and a deployed state, respectively;

FIG. 9D is a schematic plan view illustrating the deployed state of the implant of FIG. 9A used in a method for interbody fusion according to the teachings of the present invention;

FIG. 10A is an isometric view of a modified form of the implant of FIG. 9A shown in a deployed state;

FIG. 10B is a schematic plan view illustrating the deployed state of the implant of FIG. 10A used in a method for interbody fusion according to the teachings of the present invention;

FIGS. 17A and 17B are isometric views of an orthopedic implant, constructed and operative according to an embodiment of the present invention, shown in a low profile closed state and a deployed state, respectively;

FIGS. 17C-17E are schematic isometric views illustrating an inserted state and two views of a deployed state, respectively, of the implant of FIGS. 17A and 17B used in a method for spinous process distraction according to the teachings of the present invention.

DESCRIPTION OF THE PREFERRED EMBODIMENTS

Figure 7A:
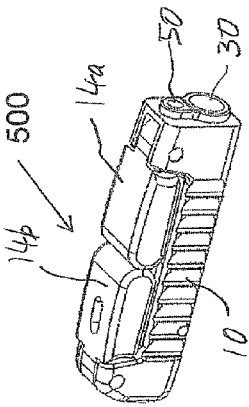
FIG. 7A is a side view of an orthopedic implant, constructed and operative according to an embodiment of the present invention, shown in a low profile closed state.

The present invention is an orthopedic implant and corresponding method in which a change of form of the implant is achieved after insertion of the implant by operation of one or more worm gear.

The principles and operation of implants and methods according to the present invention may be better understood with reference to the drawings and the accompanying description.

Referring now to the drawings, FIGS. 1A-18C show various implementations of a device for use as an orthopedic implant, constructed and operative according to selected embodiments of the present invention, in which a change of form of the implant is achieved after insertion of the implant by operation of one or more worm gear. The reference numerals introduced in the introductory description below will be used throughout the description of the various embodiments to refer to analogous features. Where more than one analogous feature appears in a given embodiment, the same reference numeral will be used with a letter suffix to distinguish the features.

In general terms, each of the devices shown has a base 10 with a length defining a direction of elongation 12 of the base and at least one arm 14, pivotally connected to base 10, typically by engagement of a pivot pin 15. Each arm 14 has a length defining a direction of elongation 16 of the arm. The device includes at least one worm gear configuration having a worm 18 mounted within base 10 so as to be rotatable about a central axis of the worm, and a set of gear teeth 20 associated with arm 14. The set of gear teeth 20 is deployed to sequentially engage, and be driven by, the worm, such that, when the worm 18 is rotated about its central axis, the arm 14 is driven through a range of pivotal motion relative to the base so as to change an angle of inclination between the direction of elongation 16 of the arm 14 and the direction of elongation 12 of the base 10.

In certain preferred embodiments, the worm (or one of a plurality of worms) is located at or near a proximal end of the base, i.e., with at least part of the worm lying within 20% of the length of the base from the proximal end of the base. In such cases, certain particularly preferred implementations of the invention employ a worm which is hollow along at least part of its length so as to define part of a filling channel for introducing biocompatible material into the orthopedic implant.

In certain preferred embodiments, the worm (or one of a plurality of worms) is located in a distal half of the base, i.e., with the worm lying within 50% of the length of the base from the distal end of the base. In such cases, rotation of the distally-located worm is achieved either by integration of the worm with a core element extending along the length of the base or by use of an elongated tool, such as a hex key or screwdriver, inserted along an access channel through the base. These implementations facilitate a range of geometrical configurations and clinical procedures which would not be possible with only a proximally-located worm, as will be exemplified below.

In certain preferred embodiments, a pair of worms, typically deployed coaxially along the base, is used to deploy two or more arms.

Specific non-limiting examples of all of the above aspects of the invention, and other innovative features, will be presented below with reference to specific drawings.

Before addressing features of the preferred embodiments in more detail, it will be helpful to define certain terminology as used herein in the description and claims. The term "worm" is used herein in the description and claims to refer to a rotatable element with a helical thread or groove. The "worm" is used as part of a "worm gear configuration" in which an adjacent arm with teeth engaging the worm is rotated by operation of the worm to rotate around a pivot axis perpendicular to a central axis of the worm. Where the worm is part of an elongated structure extending axially beyond the region of the helical groove, the term "worm" is used to refer only to the region in which the helical groove engages the adjacent teeth.

The term "handedness" is defined herein as the property of a helix or helical channel of being either right-handed (like a normal screw thread) or left-handed (like a reverse screw thread).

The "inclination" between two lines is defined herein as the angle formed by one line relative to an intersecting line which is parallel to the second line, even if actual lines do not intersect or are even non-coplanar.

Where reference is made to introducing a biocompatible material "into" the implant, it should be noted that this includes cases where the material is introduced into, and remains within, the implant as well as cases where the material is introduced into, and passes through, the implant. In certain preferred embodiments, the implant once deployed at least partially defines an enclosed volume which may be partially or entirely filled, depending upon the intended application, by introduction of suitable biocompatible material, such as for example bone particles or other material for encouraging bone growth.

Turning now to device 100 as illustrated in FIGS. 1A-3B, this is an example in which the device has a pair of worm gear configurations including a proximal worm 18a engaging teeth 20a of a proximal arm 14a and a distal worm 18b engaging teeth 20b of a distal arm 14b. Worms 18a and 18b are here integrated into a common actuator element 22, typically in the form of a rotatable pin mounted within a corresponding elongated channel passing along a majority of the length of base 10, so that the two worms rotate together about a common central axis. Actuator element 22 is shown here retained within base 10 by a transverse retaining pin 24 which engages an annular recess 26 encircling actuator element 22, preventing it from moving axially within base 10.

Proximal worm 18a is shown here formed with a central channel 28, aligned with a corresponding opening 30 in the proximal end of base 10, thereby rendering proximal worm 18a hollow. Channel 28 here provides one or more of a number of functions. Firstly, channel 28 is preferably formed with a hexagonal (or other non-circular) cross-section such that it acts as a socket for engagement by a corresponding hex-key (or other complementary) tool (not shown) to allow application of a torque to turn the actuator element 22 with its two associated worms 18a and 18b. Additionally, after reaching the desired degree of deployment and removing the tool, channel 28 forms part of a channel for introducing a biocompatible material into the implant. For this purpose, a medial region of actuator element 22 is preferably formed with lateral openings 32, which form a contiguous filling channel with opening 30 and channel 28, thereby allowing introduction of biocompatible material into interior volumes, enclosed volumes and/or spaces adjacent to the orthopedic implant.

In the example shown here, a displaceable element 34 is interconnected with a region of arms 14a and 14b in the half of the arms further from the connection with base 10, and typically near the ends of the arms. In the case shown here, displaceable element 34 is a rigid bridging element interconnected to arms 14a and 14b via a pin-and-slot engagement. Specifically, each of the arms is shown here with a laterally (here bilaterally) projecting pin 36 which engages corresponding slots 38 in displaceable element 34. It will be appreciated that this engagement can be reversed, and/or the arms may be forked and pass externally to a central bridging element.

Proximal and distal worms 18a and 18b preferably have opposing helical handedness and are configured such that, on rotation of actuator element 22 as illustrated by arrow 40 in FIG. 1B, proximal and distal arms 14a and 14b are driven simultaneously in opposing rotation. The pitch of the worms and the geometry of the worm gear configuration are typically, although not necessarily, equivalent, resulting in equal and opposite angular rotation of the two arms. This opens the device progressively to reach the deployed state of FIGS. 2A and 2B, and if continued, to the fully deployed state of FIGS. 3A and 3B. In these open states, base 10, arms 14a and 14b and bridging element 34 define an encompassed internal volume 48 which, depending on the application, may be filled with filler material during a surgical procedure. Additionally, depending upon the application, openings may be provided through base 10 (opening 42), arms 14a and 14b (openings 44) and bridging element 34 (opening 46). These openings preferably provide a contiguous path through the implant (see dashed arrows in FIG. 3B) for cases in which ingrowth of tissue and/or formation of a bone bridge through the implant parallel to the plane of expansion is desired.

The geometry of the worm gear configuration is such that arms 14a and 14b are locked at all stages of deployment. In other words, due to frictional locking of the teeth 20a, 20b within the corresponding worm grooves, force applied to the arms will not rotate the worms. The implant is thus stable in all states, and can be opened to a greater or lesser degree according to the requirement of each particular case while ensure structural stability and load-bearing capabilities in whatever state the device has reached.

The available range of angular displacement of the arms may vary between implementations. In most cases, the initial insertion state has the direction of elongation of the arms near parallel (e.g., inclined by no more than 20 degrees) to the direction of extension of base 10, thereby forming a compact form for insertion in a minimally invasive procedure. A fully deployed state of each arm is typically at an inclination of at least 30 degrees, and may reach angles of 60 degrees or even 90 degrees. In certain implementations, as exemplified below in FIGS. 7A-8B, the range of angular motion may also exceed 90 degrees, going from a compact inwardly folded insertion state to an outwardly-splayed configuration.

In the embodiment illustrated here, a threaded bore 50 allows detachable engagement between a threaded holder (not shown) and the device during introduction of the device into the body and manipulation into the desired position. One or more tool (not shown) for actuating the worm(s) may be part of an integrated delivery system together with the holder, or may be an independent tool introduced separately.

Turning now to FIGS. 4A and 4B, these illustrate a device 200 according to a variant embodiment of the present invention. Device 200 is generally very similar to device 100 described above except that, in this case, worms 18a and 18b are independently rotatable. As above, proximal worm 18a is formed with a central channel 28 which in this case additionally facilitates access via proximal the channel with a suitable tool to an engagement feature, such as a screwdriver slot 52, to allow rotation of the distal worm 18b. Proximal worm 18a is controlled by a suitable key element engaging the internal surface of channel 28, as described above. Most preferably, a tool for controlling adjustment of the implant includes a pair of concentric elements that allow simultaneous adjustment of both worms.

The ability to control the worms individually allows for one arm to be opened to a greater or lesser extent than the other. Most preferably, reverse handedness of the worms is still used in order to allow equal opening of the two arms when the two engagement elements are rotated together. The ability to achieve a variable degree of opening of each arm individually is particularly useful in a range of procedures. By way of example, if used as an upright expanding cage structure between adjacent vertebral endplates, the independent adjustment allows the surgeon to choose a suitable combination of intervertebral height restoration plus lordotic (or scoliosis) correction.

In all other respects, the structure and function of device 200 will be understood by analogy to device 100 described above.

Turning now to FIGS. 5A-5E, these illustrate further devices 300 and 350 according to further embodiments of the present invention. In this case, a single arm 14 is displaced by a single worm gear configuration displaces a displaceable element 54 which is itself pivotally interconnected with base 10. A further distinction between these embodiments and device 10 is that the initial state of arm 14 is here extending from outwards towards an extremity of base 10 rather than towards the center of the base. The effect of this structure is to provide an adjustable angle between outward facing surfaces of displaceable element 54 and base 10, for example, suited to lordotic or scoliosis correction. In such applications, the upper and lower surfaces of the devices as shown here are preferably provided with suitable projections (e.g., pyramids, ridges etc.) for engaging the vertebral endplates, as is known in the art.

In the case of device 300, the worm gear configuration is located in the proximal region of base 10. In this case, a hollow worm 18 is used, with structure and function analogous to that of worm 18a of device 100 described above.

In the case of device 350, the worm gear configuration is located in the distal half of the base. In this case, actuation of the worm may be either by insertion of an actuating tool along an open channel through base 10 (analogous to operation of worm 18b of device 200), or else the worm may be integrated with a hollow rotatable plug 56 with a proximal shaped socket for allowing operation by a suitable key.

FIGS. 6A-6F illustrate a device 400 according to a further embodiment of the present invention. Device 400 is a double worm gear implementation analogous in structure and function to device 100 described above, except that arms 14a and 14b in this case assume an initial state extending outwards from base 10 and undergo inwards rotation (arrows 58) in order to displace the bridging element 34, which is in this case longer than base 10.

One particularly preferred but non-limiting exemplary application for device 400 is illustrated schematically in. FIGS. 6E and 6F where the device is inserted laterally into the anterior area of a vertebral disc space (represented by outline 60) and expanded posteriorly, for example, as part of an interbody fusion procedure. The use of a base 10 shorter than bridging element 34 renders the footprint of this structure particularly suitable for this application. In this and all other two-worm-gear implementations, both options of linked worm gears for simultaneous deployment and independent worm gears for independent adjustment may be implemented. FIG. 6E shows schematically a holder 62 employed for introducing and positioning the device, as mentioned above.

Figure 7C:
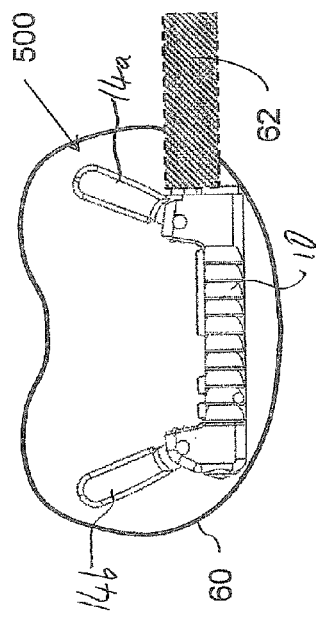
FIGS. 7B and 7C are isometric views of the implant of FIG. 7A shown in a low profile closed state and a deployed state, respectively.
Figure 7B:
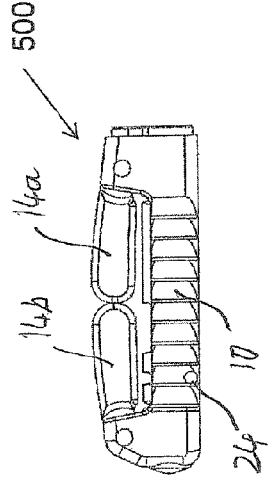

Turning now to FIGS. 7A-7D, these illustrate a device 500 according to a further embodiment of the present invention. Device 500 is fully analogous in structure and function to device 100 described above except that device 500 does not include a bridging element, and has a range of angular displacement of arms 14a, 14b greater than 90 degrees. FIG. 7C illustrates schematically an application of device 500 similar to FIGS. 6E and 6F.

Figure 7D:
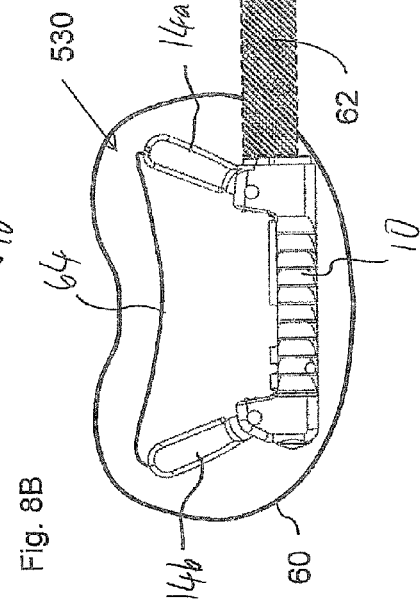
FIG. 7D is a schematic plan view illustrating the deployed state of the implant of FIG. 7A used in a method for interbody fusion according to the teachings of the present invention.
Figure 8A:
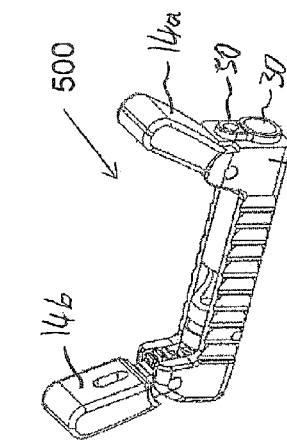
FIG. 8A is an isometric view of a modified form of the implant of FIG. 7A shown in a deployed state.
Figure 8B:
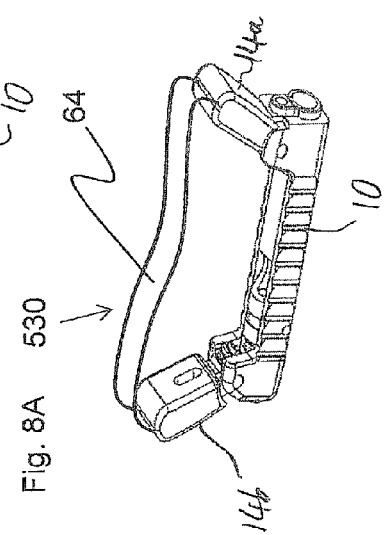
FIG. 8B is a schematic plan view illustrating the deployed state of the implant of FIG. 8A used in a method for interbody fusion according to the teachings of the present invention.

FIGS. 8A and 8B are views equivalent to FIGS. 7C and 7D, respectively, illustrating a device 530. Device 530 is equivalent to device 500 with addition of a flexible bridging element 64, preferably in the form of a flat strip, which helps to delineate an internal volume for containing biocompatible material during a surgical procedure, such as bone particles or other bone-growth promoting filler material during an interbody fusion procedure. In the initial low-profile configuration, the flexible strip is preferably folded between or behind the arms.

FIGS. 9A-9D and 10A-10B illustrate devices 540 and 550, which are fully analogous to devices 500 and 530, respectively. Devices 540 and 550 differ from devices 500 and 530 in that the range of motion of arms 14a and 14b is limited to an acute angle (less than 90 degrees). This renders these devices suitable for lateral insertion in a posterior portion of the intervertebral space for opening anteriorly, as illustrated schematically in FIGS. 9C and 10A.

Figure 11A:
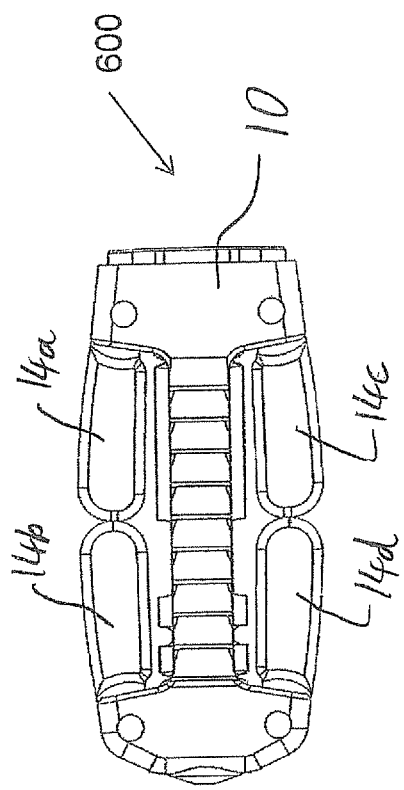
FIG. 11A is a plan view of an orthopedic implant, constructed and operative according to an embodiment of the present invention, shown in a low profile closed state.
Figure 11B:
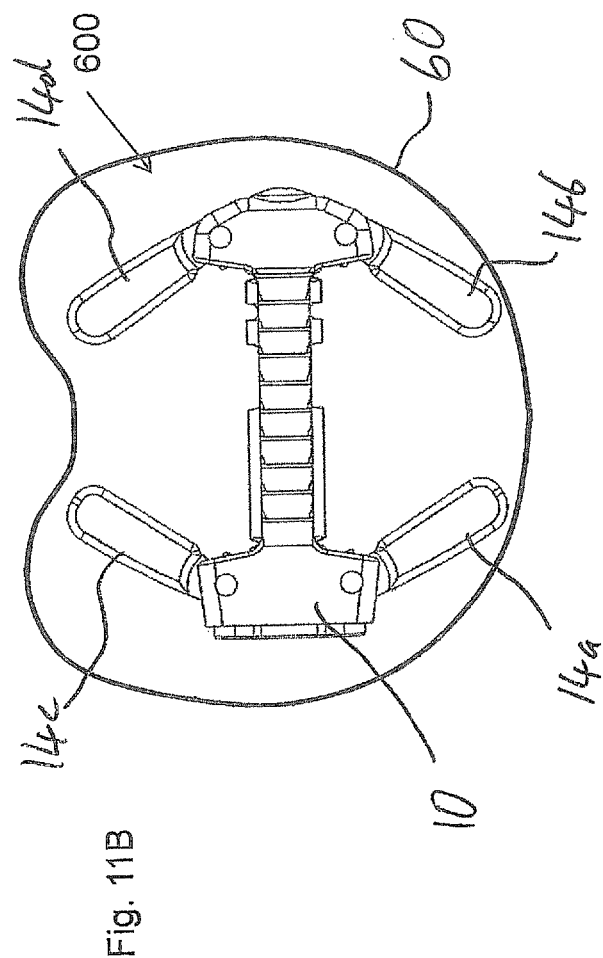
FIG. 11B is a schematic plan view illustrating the deployed state of the implant of FIG. 11A used in a method for interbody fusion according to the teachings of the present invention.

Turning now to FIGS. 11A and 11B, these illustrate a further device 600, constructed and operative according to an embodiment of the present invention. In this case, at least one, and preferably both, worm gear configurations controls an additional arm 14c, 14d pivotally connected to base 10, deployed on the opposite side of base from arms 14a and 14b. Arms 14c and 14d each has a set of gear teeth (not shown) analogous to those of the arms 14a and 14b, deployed to sequentially engage, and be driven by, the corresponding worm. As a result of this structure, rotation of the proximal worm about its central axis results in pair of opposing arms 14a and 14c being driven simultaneously through a range of pivotal motion in opposite directions. Similarly, rotation of the distal worm about its central axis results in pair of opposing arms 14b and 14d being driven simultaneously through a range of pivotal motion in opposite directions. As before, depending on the intended application, the two worms may be interconnected so as to be driven simultaneously, or may be independently adjustable to allow a differing degree of opening of the two pairs of arms. Here too, a flexible bridging element, such as a string, strip, webbing or the like, may be added between the arms opening on each side of the implant.

Turning now to FIGS. 12A-15B, these illustrate schematically a number of applications of the present invention. The device 700 used to illustrate these embodiments is essentially the same as device 400 described above, but with the dimensions of base 10 increased to be approximately the same length as bridging element 34.

Figure 12A:
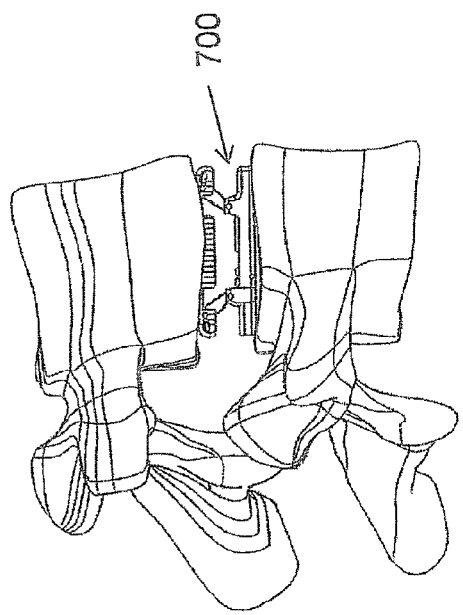
FIGS. 12A and 12B are schematic lateral views illustrating the inserted state and deployed state, respectively, of an implant according to the teachings of an embodiment of the present invention used in a method for interbody fusion with intervertebral height restoration according to the teachings of the present invention.
Figure 12B:
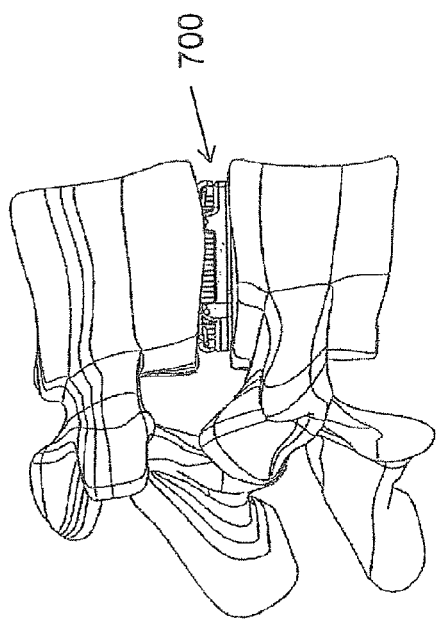

FIGS. 12A and 12B illustrate schematically an intervertebral expanding cage implementation in which one or two such devices are introduced through an anterior, posterior or TLIF approach in the collapsed state (FIG. 12A) and actuated to assist in achieving a desired degree of intervertebral height restoration (FIG. 12B) and/or lordotic correction (where the worm gear configurations are separately controllable).

Figure 13A:
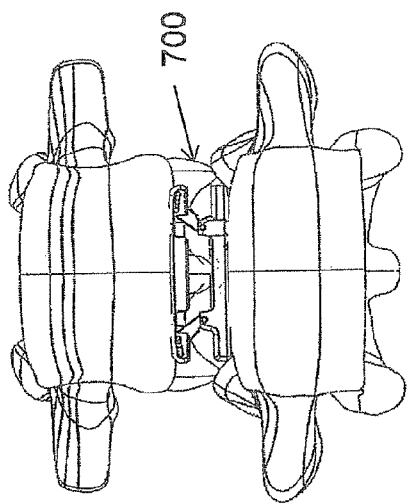
FIGS. 13A and 13B are schematic anterior views illustrating the inserted state and deployed state, respectively, of an implant according to the teachings of an embodiment of the present invention used in a method for interbody fusion with intervertebral height restoration according to the teachings of the present invention.
Figure 13B:
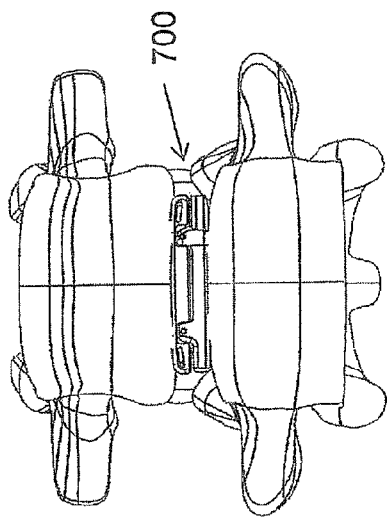
Figure 14B:
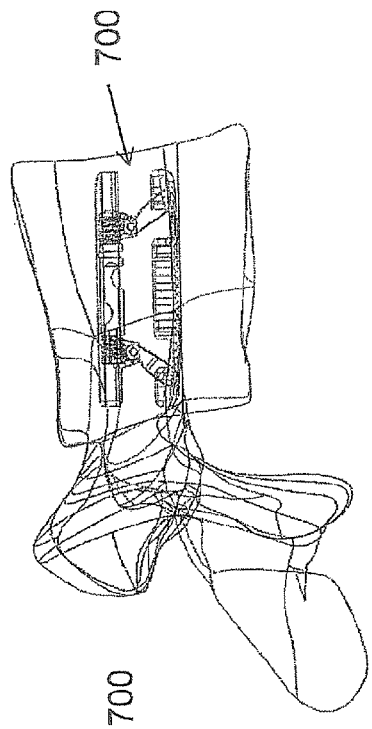
FIGS. 14A and 14B are schematic lateral views illustrating the inserted state and deployed state, respectively, of an implant according to the teachings of an embodiment of the present invention used in a method for treatment of a vertebral compression fracture (VCF) according to the teachings of the present invention.

FIGS. 13A and 13B illustrate schematically an intervertebral expanding cage implementation in the device is introduced via a lateral approach in the collapsed state (FIG. 13A) and actuated to assist in achieving a desired degree of intervertebral height restoration (FIG. 13B) and/or scoliosis correction (where the worm gear configurations are separately controllable).

Figure 15B:
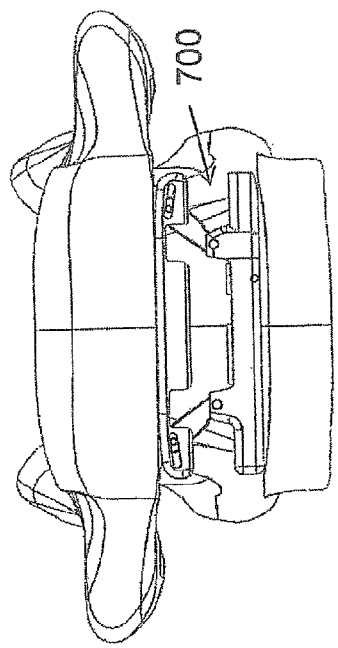
FIGS. 15A and 15B are schematic anterior views illustrating the inserted state and deployed state, respectively, of an implant according to the teachings of an embodiment of the present invention used in a method for VCF treatment according to the teachings of the present invention.
Figure 14A:
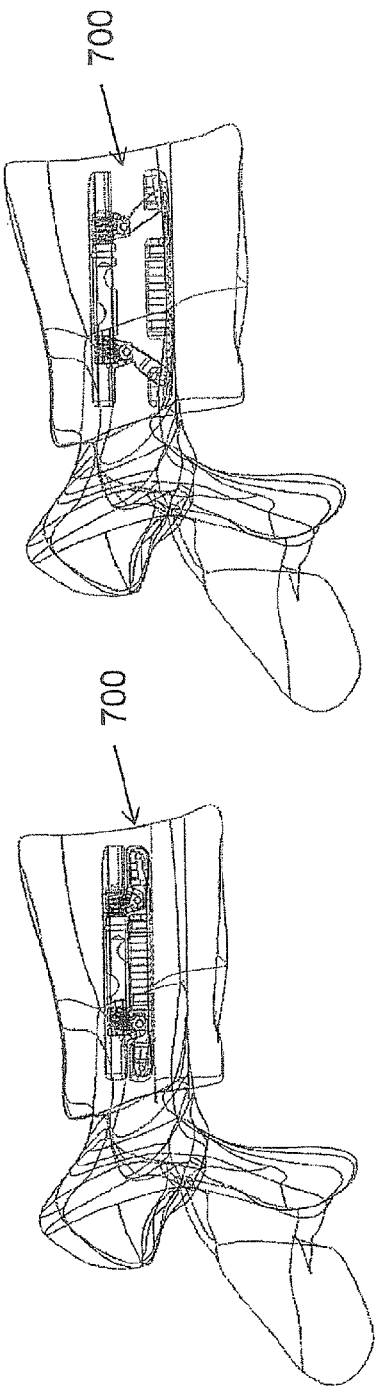
Figure 15A:
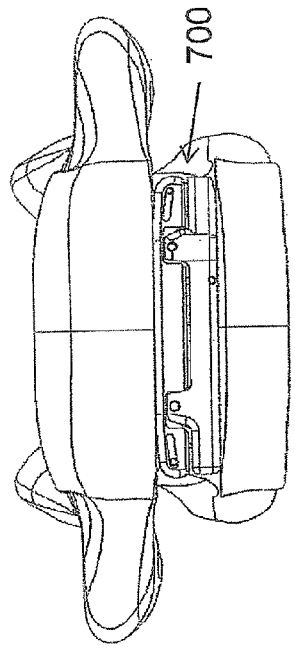

FIGS. 14A-15B illustrate an application in which the device is used for restoring vertebral body height in a vertebral compression fracture (VCF). The device is inserted into the vertebral body in the retracted state and expanded in the cranial/caudal direction. FIGS. 14A-14B illustrate an implementation via a trans pedicular approach, while FIGS. 15A-15B illustrate a lateral approach. These drawings are highly schematic, and the size of the device in the figures is not to scale and may be smaller than the vertebral body dimensions.

Figure 16B:
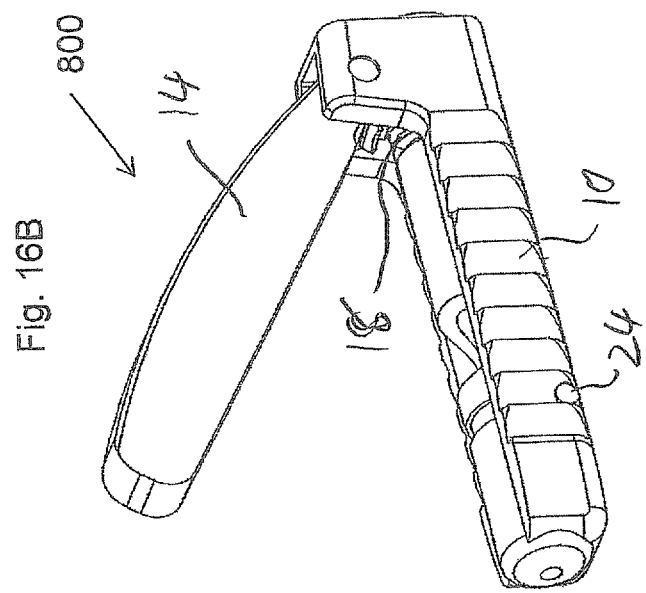
FIGS. 16A and 16B are isometric views of an orthopedic implant, constructed and operative according to an embodiment of the present invention, shown in a low profile closed state and a deployed state, respectively.
Figure 16A:
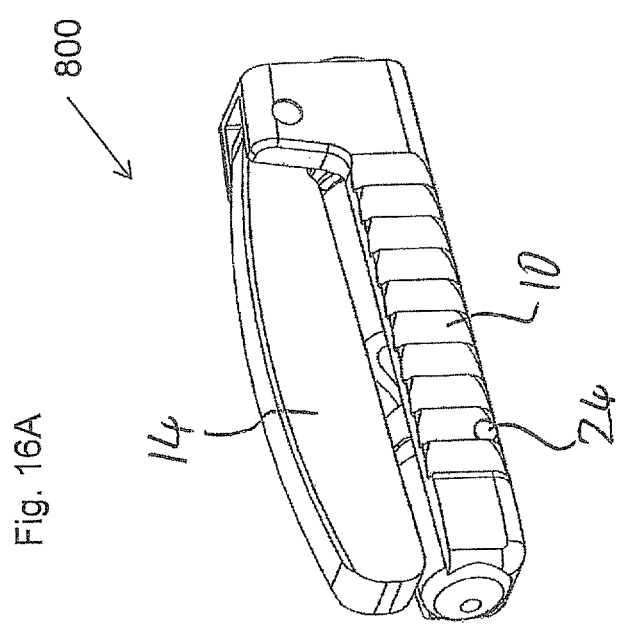

Turning now to FIGS. 16A and 16B, these show a device 800 according to an embodiment of the present invention in which arm 14 itself has one or more tissue contact surface and is rotated to create a lordotic angle relative to the lower contact surface of base 10. In the case illustrated here, the worm is deployed near the proximal end of the base, although reverse configurations with the worm and pivot axis at the distal end may also be implemented.

FIGS. 17A-17E illustrate a device 900 which is essentially similar to device 800 but adapted by addition of shaped recesses or notches 902 configured for engaging bony structures, in particular, adjacent spinous processes. Device 900 is inserted between spinous processes in a collapsed state, as shown in FIG. 17C, and then expanded to increase the distance between the spinous processes, as illustrated in FIGS. 17D and 17E. The shape of notches 902 is configured to engage the upper and lower adjacent spinous processes, thereby rendering the expanded structure stably retained between adjacent spinous processes.

Figure 18A:
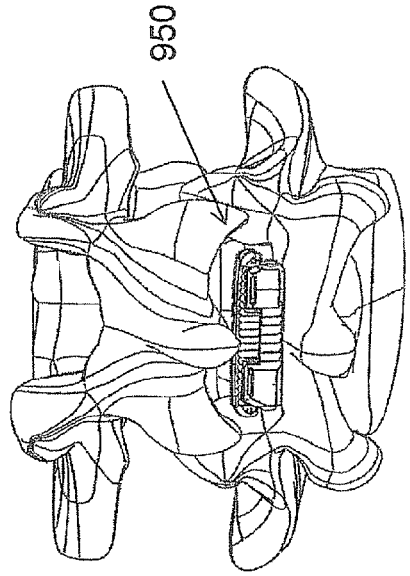
FIGS. 18A-18C are schematic isometric views illustrating two views of an inserted state and a view of a deployed state, respectively, of an implant according to the teachings of the present invention, used in a method for spinous process distraction according to the teachings of the present invention.
Figure 18B:
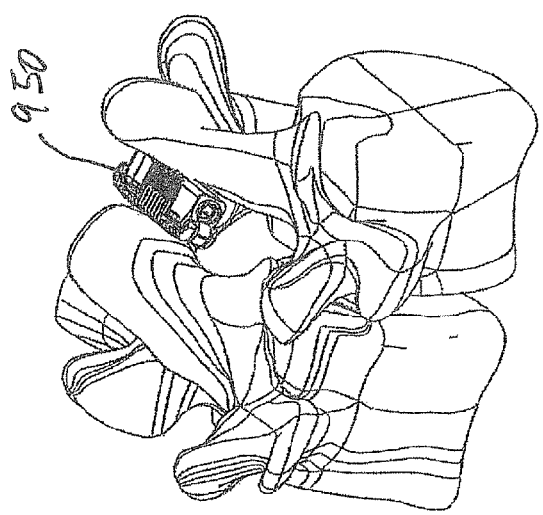
Figure 18C:
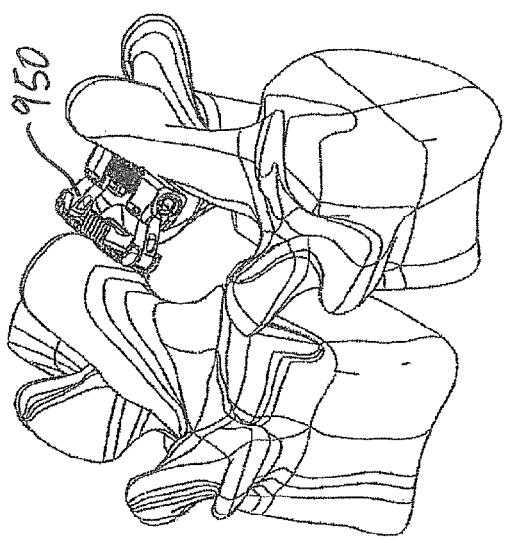

Finally, FIGS. 18A-18C illustrate an alternative device 950 for use in a spinous process distraction application analogous to that illustrated in FIGS. 17C-17E. In this case, the device is similar to device 400 and 700 described above, and employs parallel expansion between base 10 and bridging element 34 to perform the spinous process distraction.

It is understood that the teeth/ridges/pyramids may be included on the surfaces (of any/all embodiments shown) that come in contact with bony tissue in order to minimize migration and/or improve fixation of the device to the anatomy.

It will be appreciated that the above descriptions are intended only to serve as examples, and that many other embodiments are possible within the scope of the present invention as defined in the appended claims.

What is claimed is:

1. A device comprising:
   (a) a base having a length defining a direction of elongation of said base;
   (b) a first arm pivotally connected to said base, said first arm having a length defining a direction of elongation of said first arm;
   (c) a second arm pivotally connected to said base, said second arm having a length defining a direction of elongation of said second arm; and
   (d) a worm gear configuration comprising:
      (i) a worm element mounted within said base so as to be rotatable about a central axis of said worm element, said worm element comprising first and second worms rigidly interconnected by a shaft, and
      (ii) first and second sets of gear teeth associated respectively with said first and second arms, said first set of gear teeth being deployed to engage, and be driven by, said first worm, and said second set of gear teeth being deployed to engage, and be driven by, said second worm, such that, when said worm element is rotated about its central axis, said first and second arms are driven through a range of pivotal motion relative to said base so as to change an angle of inclination between said respective directions of elongation of said first and second arms and said direction of elongation of said base, wherein the device is at least part of an orthopedic implant, and wherein said worm element is formed with an internal channel extending through said first worm and along at least part of said shaft, and wherein said shaft is provided with lateral openings interconnecting with said internal channel so as to define a continuous filling channel extending through said first worm, along said shaft and laterally outwards for introducing biocompatible material into said orthopedic implant.

2. The device of claim 1, wherein said first arm has a region distanced from said pivotal connection by at least half said length of said arm, and wherein said second arm has a region distanced from said pivotal connection by at least half said length of said second arm, the device further comprising a displaceable element, said displaceable element being interconnected with said regions of said first and second arm via a pin-and-slot engagement such that displacement of said first and second arms through said range of pivotal motion from an initial position towards a final position causes displacement of said displaceable portion away from said base.

3. The device of claim 1, wherein said first and second worms have opposing helical handedness and are configured such that, on rotation of said worm element, said first and second arms are driven simultaneously in opposing rotation.

4. The device of claim 1, wherein said first arm has a region distanced from said pivotal connection by at least half said length of said arm, and wherein said second arm has a region distanced from said pivotal connection by at least half said length of said second arm, the device further comprising flexible bridging element connected to said region of said first arm and to said region of said second arm.

5. The device of claim 1, wherein said shaft is provided with a plurality of said lateral openings angularly distributed about said central axis of said worm element.

6. The device of claim 1, wherein said shaft is provided with at least two of said lateral openings, said lateral openings being staggered axially along said shaft and angularly offset about said central axis of said worm element.

* * * * *